United States Patent [19]  
Seymour

[11] 4,340,043  
[45] Jul. 20, 1982

[54] ADHESIVE-COATED SHEET MATERIAL INCORPORATING ANTI-BACTERIAL SUBSTANCES

[75] Inventor: Donald E. Seymour, Old Hatfield, England

[73] Assignee: Smith & Nephew Research Ltd., England

[21] Appl. No.: 198,106

[22] PCT Filed: Nov. 15, 1979

[86] PCT No.: PCT/GB79/00188

§ 371 Date: Jul. 17, 1980

§ 102(e) Date: Jul. 11, 1980

[87] PCT Pub. No.: WO80/01041

PCT Pub. Date: May 29, 1980

[30] Foreign Application Priority Data

Nov. 17, 1978 [GB] United Kingdom ............... 45058/78

[51] Int. Cl.$^3$ ...................... A61F 13/00; A61L 15/00
[52] U.S. Cl. ................................ 128/132 D; 128/156; 128/260
[58] Field of Search ................... 128/132 D, 155–156, 128/260

[56] References Cited

U.S. PATENT DOCUMENTS 2,427,022 9/1947 Russ et al.  
3,598,123 8/1971 Zaffaroni .............................. 128/156  
3,624,224 11/1971 Wei et al. ............................. 128/156  
3,645,835 2/1972 Hodgson ........................ 128/132 D  
3,731,683 5/1973 Zaffaroni .............................. 128/260  
3,969,498 7/1976 Catania et al.

FOREIGN PATENT DOCUMENTS 685805 12/1939 Fed. Rep. of Germany .  
1925348 11/1970 Fed. Rep. of Germany .  
811222 4/1937 France .  
2012584 3/1970 France .  
2184498 12/1973 France .  
2368962 5/1978 France .

Primary Examiner—C. Fred Rosenbaum  
Attorney, Agent, or Firm—Jacobs & Jacobs

[57] ABSTRACT

Adhesive-coated liquid-impervious moisture-vapor-permeable thin polymer sheet suitable as a wound covering has an antibacterial, preferably a solid such as silver sulphadiazine, disseminated throughout the adhesive layer, usually in amounts up to 15 wt. %, to provide uniform antibacterial properties over the wound and surrounding skin areas.

20 Claims, No Drawings

ADHESIVE-COATED SHEET MATERIAL INCORPORATING ANTI-BACTERIAL SUBSTANCES

This invention relates to sheet material used for medical purposes.

More especially this invention relates to polymeric sheet material of high moisture vapour permeability having upon one surface a layer of adhesive material which does not destroy the said permeability.

Such material is already known per se and is described in British Pat. No. 1 280 631 in general terms. It is available, for example, under the Registered Trade Mark "Op-Site". It is used as a surgical and dressing material to cover wounds (including burns) and surgical sites. In this manner it is effective to keep bacteria from the wound, and to prevent scab formation and inhibit scarring since the layer, while permeable to moisture vapour, obviously slows down the drying time of the wound.

Such material is commonly made of polyurethane sheet, e.g. Goodrich polyether polyurethane sold under the Trade Name "Estane", which can be up to three thousandths of an inch (75 microns) in thickness but is commonly less than 45 microns e.g. about 30 microns. It is coated on one surface with a continuous or discontinuous layer of suitable adhesive to approximately the same thickness. By continuous we mean that the adhesive covers the whole surface without any gaps or blank spaces; by discontinuous we mean that there is a microporous adhesive, or a pattern of lines or dots of adhesive, the pattern covering the whole surface uniformly but of course leaving occasional gaps between units of adhesive. Both of these expedients are well known in the coating art, but continuous adhesive is preferred in this context to plug any small pinholes in the sheet.

Although a sheet of material as described is effective in keeping from the wound or surgical site airborne bacteria, there remains the problem of any bacteria which happen to be present in the site or, more commonly, upon the surrounding skin. In the enclosed conditions provided by such a sheet, such bacteria can multiply unduly and lead to an infection problem.

It has been proposed to overcome this by liberal application of bacteriocidal or bacteriostatic cream or like formulation over and around the wound or surgical site. There are, however, disadvantages in this procedure since the film, if subsequently applied over this moist cream base layer, can corrugate with movement of the body and generally does not adhere.

The present invention is based upon the realisation that a bacteriostatic or bacteriocidal material can be incorporated into the adhesive layer of the sheet.

The invention accordingly consists in an adhesive-coated sheet material which is liquid-impervious but has a high moisture-vapour permeability whereby it is suitable as a wound or burn dressing, or surgical drape or like wound-covering material, wherein the adhesive coating has disseminated throughout its mass an amount of an antibacterial material sufficient to kill bacteria in the wound and surrounding covered skin area.

As well as preserving adhesion and avoiding corrugation, this invention has two advantages. Firstly, the antibacterial substance being disseminated throughout the adhesive is present in uniform known amount per unit area both over the wound and over its surroundings. Secondly, no additional substrate is needed so that the sheet can be accurately emplaced on the skin. As already stated, it then lies flat on the skin with consequent uniform water vapour transmission and bacterial barrier properties. Also avoidance of corrugations allows retention of protective and healing wound exudate over burns.

The antibacterial materials could be bacteriostatic but are usually bactericidal in nature. Various types of such materials could be used eg:

(i) metal salts, or like compounds with antibacterial metal ions, e.g. copper, mercury or silver, and optionally with additional nonmetallic ions of antibacterial properties.

(ii) typical antibiotics e.g. neomycin, soframycin, bacitracin, polymycin.

(iii) antibacterials such as chlorhexidine and its salts (iv) quaternary ammonium compounds e.g. cetrimide, domiphen bromide, polymeric quaternaries, and (v) iodophors such as povidone iodine.

The above compounds are in some instances solid materials, and in some instances liquids: moreover, some can be presented in either form. It is much preferred, however, for solid and finely divided materials to be used.

Again, some of the finely divided solids rely on the presence and activity of a relatively small atom or group such as a metal, others rely on the presence and activity of a large ionized group, and others again on both. Those utilizing metal ions are most preferable, especially if in combination with another active group.

Most preferred of all for incorporation into the adhesive layer is silver sulphadiazine in finely divided form.

We have found that up to 25% i.e., 1% to 25% (by weight of adhesive) of the antibacterial, but more preferably up to 15% by weight can be used. The lower limit can be as low as 1% but is preferably 5% for effective antibacterial properties 5% to 5% is a suitable range.

If a dispersed material, such as silver sulphadiazine, is used it is generally a so called "micronised" material. In this the state of subdivision of the material is generally speaking such that 99% of the particles are less than 20 microns in diameter and 90% less than 10 microns. In practice the majority of the particles are less, and usually considerably less, than 5 microns in diameter and are usually completely embedded in the adhesive layer. It is of no disadvantage however if some of the particles project from the adhesive layer since their antibacterial activity is thereby immediately exerted. Indeed, some particles might even bridge the layer from the outside adhesive surface to the polymer.

Although the invention as claimed is not to be construed as relying upon any hypothesis as to the mode of action, it can reasonably be inferred that some solid particles are embedded well within the adhesive coating thickness while others lie near the surface from which (depending on the relative properties of the adhesive and particles), they may protrude as such or may be separated by a thin film of polymer. Thus, when the wound-covering is applied the immediately available surface particles act forthwith to yield up their antibacterial content, whether or not this is in the form of large ions or small ions, but after this the process is conceivably controlled by ionic diffusion through the adhesive thickness in which the smaller (e.g. metal) ions are more effective. In addition to this, over the mobile and wet wound itself, as distinct from the surrounding more or less stationary and static skin, conditions may be to plasticize the adhesive layer and improve migration of the antibacterial.

Whatever the reasoning the results are not predictable in detail, some antibacterials giving less effective results than might have been expected and others more effective results. In particular silver sulphadiazine, notwithstanding its dissemination throughout a water-insoluble adhesive and its own innate water-insolubility gives interesting and valuable results.

As before, the polymer sheet is preferably polyurethane and can be up to 75 microns in thickness. More preferably it is 40 microns or less, for example about 30 microns.

The adhesive is usually a polyvinyl ether but is possibly an acrylic adhesive and can also be up to 75 microns in thickness, but is preferably less than 40 microns and usually about 30 microns in thickness.

In the field of medical products high specifications of uniformity, safety, non-toxicity and comfort must be met. The preferred products of the invention have been assessed in various respects, as itemized below, and found to be improved or not significantly deteriorated.

Thus, for example, it was found that even keeping the total adhesive weight (gms/sq.meter) more or less uniform at different silver sulphadiazine loadings the resultant changes in thickness and uniformity were still within acceptable limits. Also, even after ethylene oxide sterilization, and optionally forced aging, or gamma-irradiation the permeability of these dressings at different percentage loadings of silver sulphadiazine to water vapours, oxygen or carbon dioxide was not significantly changed. Similar results were obtained for tensile and elastic tests, that is to say, no significant differences. Adhesive properties differed slightly after gamma-irradiation for sterilising, but this is an effect on the adhesive (rather than due to the incorporation of silver sulphadiazine) and in any case is not in respect of the adhesion to moist skin.

One area of slight difference is in light-fastness. The sterilization procedures mentioned above can cause some slight discoloration, but not enough to render the film opaque so that the wound cannot be observed. This is probably a consequence of the use of a silver salt, although the film itself is known to discolour upon exposure to sunlight. Nonetheless, rapid stock turnover minimises this problem.

The invention will be further described with reference to the following Examples.

EXAMPLE 1

The adhesive formulation was made up as follows, to a solid content of 30%:

|  | g |
|---|---|
| Bakelite EHBM | 134.5 |
| Bakelite EHBC | 58.8 |
| Kelrez 42463 | 24.0 |
| Nonox WSL (antioxidant) | 1.4 |
| Toluene | 53.8 |
| SBP 2 | 96.9 |
| (standard Petroleum spirit) | |

Bakelite Resin EHBM is a poly (vinyl ethyl ether) high viscosity resin having 25% non-volatiles in hexane, a reduced viscosity at 20° C. of 4.0±0.5; a plasticity of 1.6 to 2.0 m.m; a flash point <20° F.; a specific gravity of 0.7299 and a weight per gallon of 6.07 lbs.

Bakelite Resin EDBC is a poly (vinyl ethyl ether) low viscosity resin having 98% non-volatiles; a reduced viscosity of 20° C. of 0.3±0.1; and a specific gravity at 20° C. of 0.973.

Kelrex ZR142 is a zinc resinate formed by the interaction of zinc oxides with the resin acids in partially dimerised Colophony, contains 9.6% zinc and has a melting point of 160° to 165° C.

Into the above formulation was incorporated 1% of silver sulphadiazine, which is, on a dry basis, 590 milligrams per 100 grams of the mass.

The resulting adhesive was knife-spread on to the 25-micron polyurethane film and was thereafter air-dried for two hours at ambient temperature. A disc of the adhesive-coated film incorporating the silver sulphadiazine, 17 millimeters in diameter was cut and placed adhesive side down on to neomycin assay agar plates preseeded with either *Bacillus subtilis* or *Pseudomonas aeruginosa*. The plates were left at room temperature for approximately half an hour and then incubated overnight at the optimum temperature for growth. After incubation the zones of inhibited growth around the discs were measured. In each case there was a halo of destruction of the bacteria around the edges of the disc.

EXAMPLE 2

The above experiment was repeated except that 10% by weight of the silver sulphadiazine was incorporated into the adhesive. The results, using the same-sized discs as in Example 1, were (for *Bacillus subtilis*) a 34-millimeter diameter zone of inhibition and (for *Pseudomonas aeruginosa*) a 28.9 millimeter diameter zone, in each case including the diameter of the disc.

EXAMPLE 3

A comparative test was carried out on surgical drape samples containing zero (control) 5% and 10% by weight (nominal) of silver sulphadiazine (SSD) in the adhesive, as follows:

|  | 83 Control Pts. by wt. | Nominal 5% SSD Pts. by wt. | Nominal 10% SSD Pts. by wt. |
|---|---|---|---|
| Bakelite EHBM | 36.4 | 36.4 | 36.4 |
| Bakelite EHBC | 15.9 | 15.9 | 15.9 |
| Kelrez 42463 | 6.5 | 6.5 | 6.5 |
| Nonox WSL | 0.4 | 0.4 | 0.4 |
| Toluene | 14.6 | 14.6 | 14.6 |
| SBP 2 | 26.2 | 26.2 | 26.2 |
| S.S.D. | NIL | 1.5 | 3.0 |

The solids content of the adhesive prior to spending is 30%. Thus, each sample contained 100 g of solution (30 gms solids) plus the additional SSD content. Therefore, the nominal 5% sample contained 4.8 wt.% SSD and the nominal 10% sample contained 9.1 wt.% SSD. 1 Kg weights of masses were made by the following procedure:

1. Toluene and S.S.D. powder were mixed at high speed for 5 minutes.
2. The speed was reduced to slow and Kelrez and Nonox added over 10 minutes.
3. Mixing continued for 20 minutes.
4. Addition of EHBC resin carried over 10 minutes.
5. Addition of EHBM resin carried over 20 minutes.

6. SBP2 was added.
7. Mixing continued for further 50 minutes.
Total mixing time = 2 hrs.

A 23 micron layer of adhesive was spread onto a 25 micron polyurethane film using a conventional adhesive spreading tunnel and the film cut into surgical drapes. The adhesive weight was approximately 30 grams per square meter.

Various physical and chemical tests were conducted in the samples but no significant differences in physical properties (e.g. gas and moisture permeability, adhesion, and tensile strength) were noted. The samples incorporating SSD also withstood ageing and sterilization treatments to a similar extent to the control sample.

The samples were then subject to microbiological evaluation with respect to a variety of bacterial challenges.

Samples of drapes, after ethylene oxide sterilisation, were tested by the zone diffusion technique. Discs of Opsite were placed with the adhesive down on neomycin assay agar plates, preseeding with challenge organisms. After incubation, the plates were examined and zones of inhibited growth around the samples measured.

The diameter of the discs was 10 mm, and the diameter of the inhibited zones around (and including) the discs was as follows:

| Content of S.S.D. % | Zone diameter (mm) including Opsite | | |
|---|---|---|---|
| Test organism | 0 | 5 | 10 |
| Staph. aureus | 11.9 | 13 | 15.2 |
| Ps. aeuruginosa | no zone | I | 13.8 |
| Eschericia coli | no zone | 13 | 14 |
| Candida albicans | no zone | I | I |
| Bacillus subtilis | no zone | I | 15.7 |

I No Zone around dressing but growth inhibited beneath samples.

I claim:

1. An adhesive-coated sheet material which is liquid-impervious but has a high moisture vapor permeability whereby it is suitable as a wound or burn dressing, surgical drape, or like wound-covering material, which comprises a suitable sheet having coated on one surface thereof a continuous layer of an adhesive which has incorporated thereinto in a uniform known amount per unit area an amount of an antibacterial silver salt sufficient to kill bacteria in the wound and surrounding covered skin area.

2. A sheet material according to claim 1 wherein the silver salt is in finely divided solid form.

3. A sheet material according to claim 1 in which the silver salt is silver sulphadiazine.

4. A sheet material according to claim 1 wherein the amount of silver salt is from 1 to 25% by weight based on the weight of the adhesive.

5. A sheet material according to claim 4 wherein the amount is from 5 to 15% by weight.

6. A sheet material according to claim 1 wherein the silver salt is particulate and the majority of the particles are less than five microns in diameter.

7. A sheet material according to claim 1 wherein the sheet is polyurethane up to 75 microns in thickness.

8. A sheet material according to claim 1 in which the adhesive is a layer of a polyvinyl ether up to 75 microns in thickness.

9. A sheet material according to claim 7 or 8 in which each layer is up to 30 microns in thickness.

10. A sheet material according to claim 1 which additionally comprises a peelable release layer on the adhesive face, to be removed prior to use.

11. A sheet material according to claim 1, in which the adhesive layer is acrylic adhesive up to 75 microns in thickness.

12. A sheet material according to claim 1, in which adhesive layer is acrylic adhesive up to 40 microns in thickness.

13. A sheet material according to claim 1, in which the adhesive layer is acrylic adhesive up to about 30 microns in thickness.

14. A sheet material according to claim 8, wherein the layer of a polyvinyl ether is up to 30 microns in thickness.

15. A sheet material according to claim 7, in which the polyurethane sheet is 40 microns or less in thickness.

16. A sheet material according to claim 7, in which the polyurethane sheet is about 30 microns in thickness.

17. A sheet material according to claim 8 wherein the layer of a polyvinyl ether is less than 40 microns in thickness.

18. A sheet material according to claim 1 wherein the sheet material is a 25 micron polyurethane film and the adhesive consists essentially of a polyvinyl ethyl ether high viscosity resin having 25% non-volatiles in hexane, a reduced viscosity at 20° C. of 4.0±0.5; a plasticity of 1.6 to 2.0 m.m; a flash point less than 20° F.; a specific gravity of 0.7299 and a weight per gallon of 6.07 lbs.; a polyvinyl ethyl ether low viscosity resin having 98% non-volatiles; a reduced viscosity of 20° C. of 0.3±0.1; and a specific gravity at 20° C. of 0.973; a zinc resinate formed by the interaction of zinc oxides with the resin acids in a partially dimerised Colophony, containing 9.6% zinc and having a melting point of 160° to 165° C., an antioxidant, Toluene, and standard petroleum spirits into which was incorporated 1% by weight of silver sulphadiazine which is, on a dry basis, 590 milligrams per 100 grams of mass.

19. A sheet material according to claim 1 wherein the sheet material is a 25 micron polyurethane film and the adhesive consists essentially of a polyvinyl ethyl ether high viscosity resin having 25% non-volatiles in hexane, a reduced viscosity at 20° C. of 2.0±0.5; a plasticity of 1.6 to 2.0 m.m; a flash point less than 20° F.; a specific gravity of 0.7299 and a weight per gallon of 6.07 lbs.; a polyvinyl ethyl ether low viscosity resin having 98% non-volatiles; a reduced viscosity of 20° C. of 0.3±0.1; and a specific gravity at 20° C. of 0.973; a zinc resinate formed by the interaction of zinc oxides with the resin acids in a partially dimerised Colophony, containing 9.6% zinc and having a melting point of 160° to 165° C., an antioxidant, Toluene, and standard petroleum spirits into which was incorporated 10% by weight of silver sulphadiazine which is, on a dry basis, 590 milligrams per 100 grams of mass.

20. A sheet material according to claim 1 wherein the silver salt is in micronized form.

* * * * *